United States Patent
Pevarello et al.

(10) Patent No.: US 6,455,559 B1
(45) Date of Patent: Sep. 24, 2002

(54) PHENYLACETAMIDO-PYRAZOLE DERIVATIVES, PROCESS FOR THEIR PREPARATION AND THEIR USE AS ANTITUMOR AGENTS

(75) Inventors: Paolo Pevarello, Pavia (IT); Paolo Orsini, Gallarate (IT); Gabriella Traquandi, Milan (IT); Maria Gabriella Brasca, Milan (IT); Raffaella Amici, Codogno (IT); Manuela Villa, Lurago d'Erba (IT); Claudia Piutti, Cantone di Nerviano (IT); Mario Varasi, Milan (IT); Antonio Longo, Milan (IT)

(73) Assignee: Pharmacia Italia S.p.A., Milan (IT)

( * ) Notice: Subject to any disclaimer, the term of this patent is extended or adjusted under 35 U.S.C. 154(b) by 0 days.

(21) Appl. No.: 09/907,943

(22) Filed: Jul. 19, 2001

(51) Int. Cl.⁷ .................... C07D 263/04; A61K 31/422; A61P 35/00
(52) U.S. Cl. ...................... 514/376; 514/407; 548/229; 548/364.1
(58) Field of Search .............................. 548/229, 364.1 514/376, 407

(56) References Cited

U.S. PATENT DOCUMENTS

2002/0032184 A1    3/2002    Corbau et al.

FOREIGN PATENT DOCUMENTS

| WO | WO 98/52941 | * 11/1998 |
| WO | WO 01/12189 A1 | * 2/2001 |
| WO | 02/04424 A1 | 1/2002 |

OTHER PUBLICATIONS

The Peruvian Official Gazette, Lima, Feb. 21, 2002, Adviso No: 131–2002, Patente de Invencion para "Derivados de Pirazol".

* cited by examiner

*Primary Examiner*—Joseph K. McKane
*Assistant Examiner*—Kamal Saeed
(74) *Attorney, Agent, or Firm*—Oblon, Spivak, McClelland, Maier & Neustadt, P.C.

(57) ABSTRACT

Compounds represented by formula (I)

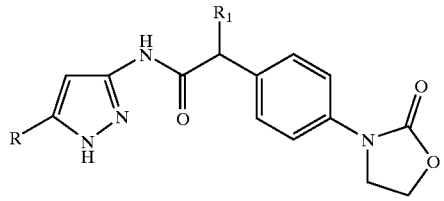

(I)

wherein R is a $C_3$–$C_5$ cycloalkyl group, $R_1$ is a hydrogen atom or a methyl group, or a pharmaceutically acceptable salt thereof; are useful in the treatment of cell proliferative disorders, e.g. cancer, associated with an altered cell cycle dependent kinase activity.

31 Claims, No Drawings

PHENYLACETAMIDO-PYRAZOLE DERIVATIVES, PROCESS FOR THEIR PREPARATION AND THEIR USE AS ANTITUMOR AGENTS

BACKGROUND OF THE INVENTION

Field of the Invention

The present invention relates to phenylacetamido-pyrazole derivatives, to a process for their preparation, to pharmaceutical compositions containing them, and to their use as therapeutic agents, particularly in the treatment of cancer and cell proliferation disorders.

Discussion of the Background

Several cytotoxic drugs such as, e.g., fluorouracil (5-FU), doxorubicin and camptothecins damage DNA or affect cellular metabolic pathways and thus cause, in many cases, an indirect block of the cell cycle. Therefore, by producing an irreversible damage to both normal and tumor cells, these agents result in a significant toxicity and side effects.

In this respect, compounds capable of functioning as highly specific antitumor agents by selectively leading to tumor cell arrest and apoptosis, with comparable efficacy but reduced toxicity than the currently available drugs, are desirable.

It is well known that progression through the cell cycle is governed by a series of checkpoint controls, otherwise referred to as restriction points, which are regulated by a family of enzymes known as the cyclin-dependent kinases (cdk). In turn, the cdks themselves are regulated at many levels such as, for instance, binding to cyclins.

The co-ordinated activation and inactivation of different cyclin/cdk complexes is necessary for normal progression through the cell cycle. Both the critical G1-S and G2-M transitions are controlled by the activation of different cyclin/cdk activities. In G1, both cyclin D/cdk4 and cyclin E/cdk2 are thought to mediate the onset of S-phase. Progression through S-phase requires the activity of cyclin A/cdk2 whereas the activation of cyclin A/cdc2 (cdk1) and cyclin B/cdc2 are required for the onset of mitosis. For a general reference to cyclins and cyclin-dependent kinases see, for instance, Kevin R. Webster et al, in Exp. Opin. Invest. Drugs, 1998, Vol. 7(6), 865–887.

Checkpoint controls are defective in tumor cells due, in part, to disregulation of cdk activity. For example, altered expression of cyclin E and cdks has been observed in tumor cells, and deletion of the cdk inhibitor p27 KIP gene in mice has been shown to result in a higher incidence of cancer.

Increasing evidence supports the idea that the cdks are rate-limiting enzymes in cell cycle progression and, as such, represent molecular targets for therapeutic intervention. In particular, the direct inhibition of cdk/cyclin kinase activity should be helpful in restricting the unregulated proliferation of a tumor cell.

SUMMARY OF THE INVENTION

It is an object of the invention to provide compounds that are useful in treating cell proliferative disorders associated with an altered cell cycle dependent kinase activity. It is another object to provide compounds that have cdk/cyclin kinase inhibitory activity.

The present inventors have now discovered that certain phenylacetamido-pyrazoles are endowed with cdk/cyclin kinase inhibitory activity and are thus useful in therapy as antitumor agents and lack, in terms of both toxicity and side effects, the aforementioned drawbacks associated with currently available antitumor drugs.

More specifically, the phenylacetamido-pyrazoles of the invention are useful in the treatment of a variety of cancers including, but not limited to: carcinoma such as bladder, breast, colon, kidney, liver, lung, including small cell lung cancer, esophagus, gall-bladder, ovary, pancreas, stomach, cervix, thyroid, prostate, and skin, including squamous cell carcinoma; hematopoietic tumors of lymphoid lineage including leukaemia, acute lymphocitic leukaemia, acute lymphoblastic leukaemia, B-cell lymphoma, T-cell-lymphoma, Hodgkin's lymphoma, non-Hodgkin's lymphoma, hairy cell lymphoma and Burkett's lymphoma; hematopoietic tumors of myeloid lineage, including acute and chronic myelogenous leukemtas, myelodysplastic syndrome and promyelocytic leukaemia; tumors of mesenchymal origin, including fibrosarcoma and rhabdomyosarcoma; tumors of the central and peripheral nervous system, including astrocytoma neuroblastoma, glioma and schwannomas; other tumors, including melanoma, seminoma, teratocarcinoma, osteosarcoma, xeroderma pigmentosum, keratocanthoma, thyroid follicular cancer and Kaposi's sarcoma.

Due to the key role of cdks in the regulation of cellular proliferation, these phenylacetamido-pyrazole derivatives are also useful in the treatment of a variety of cell proliferative disorders such as, for example, benign prostate hyperplasia, familial adenomatosis polyposis, neurofibromatosis, psoriasis, vascular smooth cell proliferation associated with atherosclerosis, pulmonary fibrosis, arthritis, glomerulonephritis and post-surgical stenosis and restenosis.

The compounds of the invention may be useful in treatment of Alzheimer's disease, as suggested by the fact that cdk5 is involved in the phosphorylation of tau protein (J. Biochem. 117, 741–749, 1995).

The compounds of this invention, as modulators of apoptosis, may also be useful in the treatment of cancer, viral infections, prevention of AIDS development in HIV-infected individuals, autoimmune diseases and neurodegenerative disorders.

The compounds of this invention may be useful in inhibiting tumor angiogenesis and metastasis.

The compounds of the invention may also act as inhibitor of other protein kinases, e.g., protein kinase C in different isoforms, Met, PAK-4, PAK-5, ZC-1, STLK-2, DDR-2, Aurora 1, Aurora 2, Bub-1, PLK, Chk1, Chk2, HER2, raf1, MEK1, MAPK, EGF-R, PDGF-R, FGF-R, IGF-R, P13K, weel kinase, Src, Abl, Akt, MAPK, ILK, MK-2, IKK-2, Cdc7, Nek, and thus be effective in the treatment of diseases associated with other protein kinases.

The compounds of the invention are also useful in the treatment and prevention of radiotherapy-induced or chemotherapy-induced alopecia.

Accordingly, the present invention provides a method for treating cell proliferative disorders associated with an altered cell cycle dependent kinase activity, by administering to a mammal in need thereof an effective amount of a phenylacetamido-pyrazole derivative represented by formula (I):

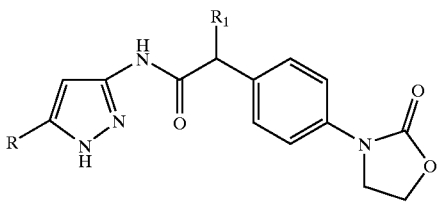

wherein

R is a $C_3$–$C_5$ cycloalkyl group;

$R_1$ is a hydrogen atom or a methyl group;

or a pharmaceutically acceptable salt thereof.

In a preferred embodiment of the method described above, the cell proliferative disorder is selected from the group consisting of cancer, Alzheimer's disease, viral infections, autoimmune diseases and neurodegenerative disorders.

Specific types of cancer that may be treated include carcinoma, squamous cell carcinoma, hematopoietic tumors of myeloid or lymphoid lineage, tumors of mesenchymal origin, tumors of the central and peripheral nervous system, melanoma, seminoma, teratocarcinoma, osteosarcoma, xeroderma pigmentosum, keratocanthoma, thyroid follicular cancer, and Kaposi's sarcoma.

In another preferred embodiment of the method described above, the cell proliferative disorder is selected from the group consisting of benign prostate hyperplasia, familial adenomatosis polyposis, neuro-fibromatosis, psoriasis, vascular smooth cell proliferation associated with atherosclerosis, pulmonary fibrosis, arthritis, glomerulonephritis and post-surgical stenosis and restenosis.

In addition, the inventive method provides tumor angiogenesis and metastasis inhibition. The inventive method may also provide cell cycle inhibition or cdk/cyclin dependent inhibition.

In addition to the above, the method object of the present invention provides treatment and prevention of radiotherapy-induced or chemotherapy-induced alopecia.

The present invention also provides a phenylacetamido-pyrazole derivative represented by formula (I):

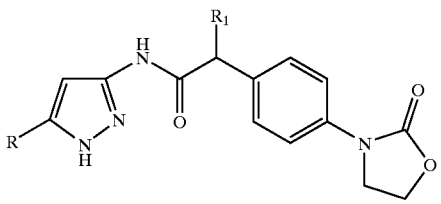

wherein

R is a $C_3$–$C_5$ cycloalkyl group;

$R_1$ is a hydrogen atom or a methyl group;

or a pharmaceutically acceptable salt thereof.

The present invention also includes methods of synthesising the phenylacetamido-pyrazole derivatives represented by formula (I). A pharmaceutical composition comprising the phenylacetamido-pyrazole derivatives represented by formula (I) is also included in the present invention.

A more complete appreciation of the invention and many of the attendant advantages thereof will be readily obtained as the same becomes better understood by reference to the following detailed description.

DETAILED DESCRIPTION OF THE INVENTION

Several carbonylamino-pyrazole derivatives are known in the art, for instance as pesticides, herbicides or even as therapeutic agents. Among these are, as an example, heteroaryl-pyrazoles active as p38 kinase inhibitors (WO 98/52941, G. D. Searle and Co.) and 3-amino-pyrazoles active as protein kinase inhibitors (WO 96/14843, COR Therapeutics, Inc.).

The international patent application WO 01/12189 in the name of Pharmacia & Upjohn S.p.A. and Pharmacia & Upjohn Co., herewith incorporated by reference, discloses a class of carbonylamino-pyrazoles further substituted by cycloalkyl groups within the pyrazole ring, which possess cell cycle dependent kinase inhibitory activity.

The compounds of the present invention fall within the scope of the general formula of WO 01/12189 but are not specifically exemplified therein.

In addition, a class of carbonylamino-pyrazoles endowed with cyclin dependent kinase inhibitory activity is also disclosed in the US provisional patent application No. 60/252911 filed on Nov. 27, 2000 in the name of Pharmacia & Upjohn S.p.A., which is herewith incorporated by reference.

As it will be readily appreciated, the unsubstituted ring nitrogen pyrazoles in the compounds of the invention are known to rapidly equilibrate, in solution, as admixtures of both tautomers:

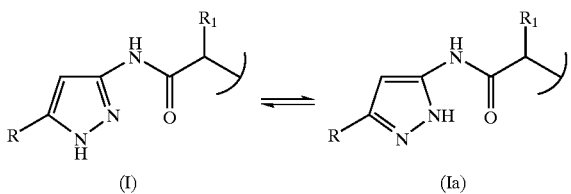

Accordingly, in the present invention and unless specifically noted otherwise, where only one tautomer is indicated for the compounds of formula (I), the other (Ia), is also within the scope of the present invention.

The compounds of formula (I) may have asymmetric carbon atoms and may therefore exist either as racemic admixtures or as individual optical isomers which are all within the scope of the present invention.

As an example, the compounds of formula (I) wherein $R_1$ is methyl have an asymmetric carbon atom and, hence, both the (R) and (S) optical isomers as well as the racemic (R,S) admixture are within the scope of the invention.

Likewise, the use as an antitumor agent of all the possible isomers and their admixtures and of both the metabolites and the pharmaceutically acceptable bio-precursors (otherwise referred to as pro-drugs) of the compounds of formula (I) are also within the scope of the present invention.

As used herein, unless otherwise specified, the term $C_3$–$C_5$ cycloalkyl comprises cyclopropyl, cyclobutyl and cyclopentyl.

Because of possible protonation reactions at a pyrazole nitrogen atom, the compounds of the invention may give rise to acid addition salts.

Pharmaceutically acceptable salts of the compounds of formula (I) include the acid addition salts with inorganic or organic acids such as, for instance, nitric, hydrochloric, hydrobromic, sulphuric, perchloric, phosphoric, acetic, trifluoroacetic, propionic, glycolic, lactic, oxalic, malonic, malic, maleic, tartaric, citric, benzoic, cinnamic, mandelic, methanesulphonic, isethionic and salicylic acid.

Preferred compounds of the invention are the compounds of formula (I) wherein R is cyclopropyl.

Another class of preferred compounds of the invention are those wherein $R_1$ is a methyl group.

Still more preferred are the compounds wherein both features are combined so as to get a compound of formula (I) wherein R is cyclopropyl and $R_1$ is methyl.

Even more preferred is the compound of formula (I) wherein R is cyclopropyl and $R_1$ is methyl, in its (S) optical form, namely (2S)-N-(5-cyclopropyl-1H-pyrazol-3-yl)-2-[4-(2-oxo-1,3-oxazolidin-3-yl)phenyl]propanamide.

Examples of compounds of formula (I) of the invention, optionally in the form of pharmaceutically acceptable salts, are:

1. N-(5-cyclopropyl-1H-pyrazol-3-yl)-2-[4-(2-oxo-1,3-oxazolidin-3-yl)phenyl]propanamide;
2. (2R)-N-(5-cyclopropyl-1H-pyrazol-3-yl)-2-[4-(2-oxo-1,3-oxazolidin-3-yl)phenyl]propanamide;
3. (2S)-N-(5-cyclopropyl-1H-pyrazol-3-yl)-2-[4-(2-oxo-1,3-oxazolidin-3-yl)phenyl]propanamide;
4. N-(5-cyclopropyl-1H-pyrazol-3-yl)-2-[4-(2-oxo-1,3-oxazolidin-3-yl)phenyl]acetamide;
5. N-(5-cyclobutyl-1H-pyrazol-3-yl)-2-[4-(2-oxo-1,3-oxazolidin-3-yl)phenyl]propanamide;
6. (2R)-N-(5-cyclobutyl-1H-pyrazol-3-yl)-2-[4-(2-oxo-1,3-oxazolidin-3-yl)phenyl]propanamide;
7. (2S)-N-(5-cyclobutyl-1H-pyrazol-3-yl)-2-[4-(2-oxo-1,3-oxazolidin-3-yl)phenyl]propanamide;
8. N-(5-cyclobutyl-1H-pyrazol-3-yl)-2-[4-(2-oxo-1,3-oxazolidin-3-yl)phenyl]acetamide;
9. N-(5-cyclopentyl-1H-pyrazol-3-yl)-2-[4-(2-oxo-1,3-oxazolidin-3-yl)phenyl]propanamide;
10. (2R)-N-(5-cyclopentyl-1H-pyrazol-3-yl)-2-[4-(2-oxo-1,3-oxazolidin-3-yl)phenyl]propanamide;
11. (2S)-N-(5-cyclopentyl-1H-pyrazol-3-yl)-2-[4-(2-oxo-1,3-oxazolidin-3-yl)phenyl]propanamide;
12. N-(5-cyclopentyl-1H-pyrazol-3-yl)-2-[4-(2-oxo-1,3-oxazolidin-3-yl)phenyl]acetamide;

The compounds of formula (I) and the pharmaceutically acceptable salts thereof, object of the invention, may be obtained by a process comprising:

a) reacting the compounds of formula (II) or the regioisomers of formula (IIa)

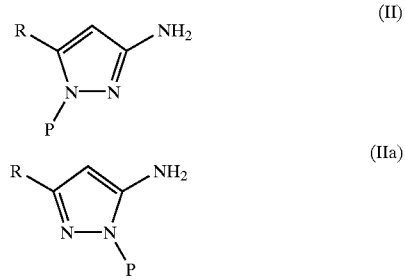

wherein R is as above defined and P represents a suitable nitrogen-pyrazole protecting group, with the compounds of formula (III)

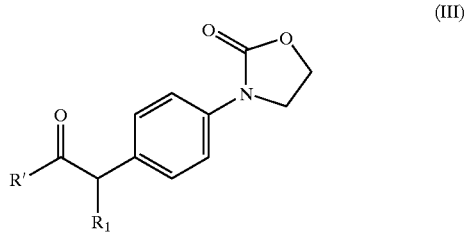

wherein $R_1$ is as above defined and R' represents hydroxy or a halogen atom, thus obtaining the compounds of formula (IV) or (IVa), respectively

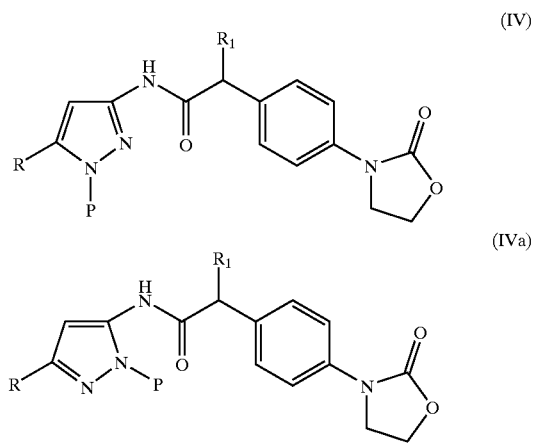

b) and deprotecting the compounds of formula (IV) or (IVa) so as to obtain the derivatives of formula (I) and, if desired, converting them into pharmaceutically acceptable salts thereof.

The above process is an analogy process which can be carried out according to well known methods.

According to step a) of the process, the reaction of the compounds of formula (II) or (IIa) with the compounds of formula (III) can be carried out in the presence of a coupling agent, for instance a carbodiimide such as 1,3-dicyclohexylcarbodiimide, 1,3-diisopropylcarbodiimide or 1-(3-dimethylaminopropyl)-3-ethylcarbodiimide, optionally in the presence of a tertiary base such as triethylamine, N-methylmorpholine, N,N-diisopropylethylamine or pyridine.

The reaction occurs in a suitable solvent such as, for example, dichloromethane, chloroform, tetrahydrofuran, diethylether, 1,4-dioxane, acetonitrile, toluene or N,N-dimethylformamide, at a temperature ranging from about −10° C. to reflux and for a suitable time, for instance from about 30 minutes to about 96 hours.

Alternatively, the reaction of the compounds of formula (II) or (IIa) with the compounds of formula (III) can be also carried out by a mixed anhydride method, that is by using an alkyl chloroformate such as ethyl, isobutyl or isopropylchloroformate in the presence of a tertiary base such as triethylamine, N-methylmorpholine, N,N-diisopropylethylamine or pyridine, in a suitable solvent such as toluene, dichloromethane, chloroform, tetrahydrofuran, acetonitrile, diethylether, 1,4-dioxane or N,N-dimethylformamide, at a temperature ranging from about −30° C. to room temperature.

When starting from the compounds of formula (III) wherein R' is a halogen atom, for instance chlorine, the reaction can be carried out in the presence of a base such as triethylamine, N-methylmorpholine, N,N-diisopropylethylamine or pyridine, in a suitable solvent such as ethyl acetate, dichloromethane, chloroform, diethylether, tetrahydrofuran, 1,4-dioxane, acetonitrile, toluene or N,N-dimethylformamide, at a temperature ranging from about 0° C. to reflux.

As far as the compounds of formula (II) or (IIa) are concerned, suitable P groups are those conventionally used to protect pyrazole-nitrogen atoms.

Preferably, for both compounds (II) and (IIa), P represents a tert-butoxycarbonyl (BOC) group.

In step b) of the process, the compounds of formula (IV) or (IVa) are converted into the desired derivatives of formula (I) by deprotecting the pyrazole-nitrogen atom, according to conventional methods. As an example, deprotection from BOC may occur by acidic hydrolysis, for instance in the presence of trifluoroacetic, formic or sulphuric acid, in a suitable solvent such as dichloromethane, 1,4-dioxane or ethanol, at a temperature ranging from about 0° C. to room temperature.

The optional salification of a compound of formula (I) or, alternatively, the conversion of a salt thereof into the free compound, can be all carried out by conventional methods.

The compounds of formula (II) or (IIa) are known compounds or may be prepared according to known methods by starting from the corresponding deprotected amino-pyrazoles.

For a reference to the preparation of the compounds of formula (II) see, for instance, the aforementioned WO 01/12189.

When preparing the compounds of formula (IIa), the R-substituted amino-pyrazoles are protected, for instance as BOC derivatives, through reaction with tert-butoxycarbonylanhydride in the presence of a dichloromethane/water admixture and of an inorganic base such as sodium hydroxide, carbonate or hydrogenocarbonate. Alternatively, this same reaction may be also carried out in dichloromethane, chloroform, toluene, tetrahydrofuran or 1,4-dioxane, and in the presence of an organic base, for instance triethylamine or N,N-diisopropylethylamine, at a temperature ranging from about 0° C. to room temperature.

Alternatively, the compounds of formula (IIa), for instance protected as BOC derivatives, can be prepared by reacting the corresponding keto-nitriles of formula (V)

(V)

wherein R is as described above, with tert-butylcarbazate in a suitable solvent such as ethanol or methanol, in the presence of a base such as triethylamine or N,N-diisopropylethylamine, at a temperature ranging from about 0° C. to room temperature.

The compounds of formula (III) wherein R' is a halogen atom, for instance chlorine, can be prepared from the corresponding derivatives of formula (III) wherein R' is hydroxy, by reacting these latter with oxalyl chloride or thionyl chloride, according to conventional methods for preparing acyl halides. The reaction may occur in the presence of a suitable solvent, for instance dichloromethane, tetrahydrofuran, ethyl acetate or toluene, at a temperature ranging from room temperature to reflux.

In their turn, the compounds of formula (III) wherein R' is hydroxy can be prepared by a process comprising reacting a derivative of formula (VI)

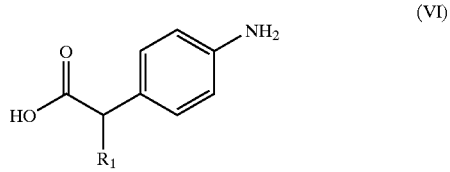

(VI)

wherein $R_1$ is as defined above, with 2-chloroethylchloroformate, followed by cyclization in a basic medium.

In particular, the reaction with 2-chloroethylchloroformate can be carried out in the presence of aqueous sodium hydroxide and toluene at room temperature, or in a suitable solvent such as dichloromethane, chloroform or tetrahydrofuran with a conventional base under anhydrous conditions, at a temperature ranging from about −20° C. to room temperature. The intermediate compounds of formula (VII) thus prepared

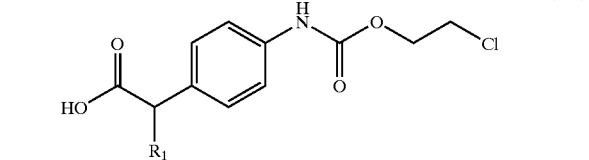

(VII)

wherein $R_1$ is as above defined, is then treated with an aqueous base, for instance sodium hydroxide, in a suitable solvent such as water or water-methanol admixtures, at a temperature ranging from room temperature to reflux or, alternatively, with an inorganic or an organic base such as potassium carbonate or 1,8-diazabicyclo[5.4.0]undec-7-ene in N,N-dimethylformamide or N,N-dimethylacetamide at room temperature.

The compounds of formula (VI) are known or can be easily prepared according to known methods. When they are enatiomerically pure, they are intended as being obtained by resolution of the racemate, according to conventional methods.

Alternatively, the compounds of formula (I) and the pharmaceutically acceptable salts thereof can be prepared by a process comprising:

a) reacting the compounds of formula (VIII)

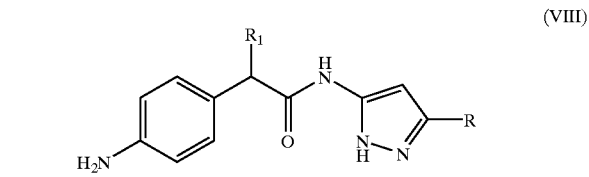

(VIII)

wherein R and $R_1$ are as described above, with chloroethylchloroformate in the presence of a base such as pyridine, triethylamine or N,N-diisopropylethylamine and in a suitable solvent such as pyridine, dichloromethane, tetrahydrofuran or N,N'-dimethylformamide, at a temperature ranging from about −20° C. to room temperature, thus obtaining the compounds of formula (IX)

(IX)

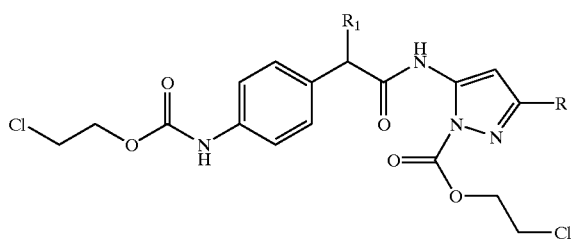

wherein R and R$_1$ are as described above;

b) reacting the compounds of formula (IX) with a suitable base such as potassium carbonate or 1,8-diazabicyclo[5.4.0]undec-7-ene in a suitable solvent such as N,N-dimethylformamide or N,N-dimethylacetamide, at a temperature ranging from room temperature to reflux, thus obtaining the compounds of formula (X)

(X)

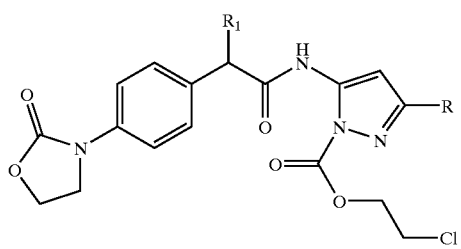

c) and by hydrolyzing the compounds of formula (X) with a base such as triethylamine or potassium carbonate in a suitable solvent such as methanol.

In their turn, the compounds of formula (VIII) can be prepared by a process comprising:
a) reacting the compounds of formula (XI)

(XI)

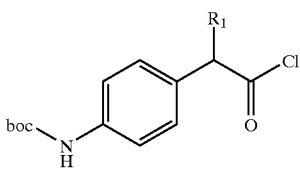

wherein R$_1$ is as described above, with the compounds of formula (IIa) wherein R is as described above, thus obtaining the compounds of formula (XII)

(XII)

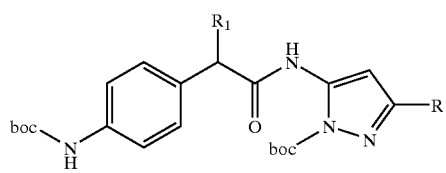

b) and by hydrolyzing the compounds of formula (XII) in acidic medium.

The reaction between the compounds of formula (XI) and the compounds of formula (IIa) can be carried out in the presence of a conventional organic base such as triethylamine, N-methylmorpholine or N,N-diisopropylethylamine, in a suitable solvent such as chloroform, dichloromethane, tetrahydrofuran or 1,4-dioxane, at a temperature ranging from about 0° C. to room temperature.

The hydrolysis of the compounds of formula (XII) to afford the compounds of formula (VIII) can be carried out in a suitable solvent such as dichloromethane or ethanol with a suitable acid such as trifluoroacetic, formic or sulphuric acid at room temperature.

The compounds of formula (XI) can be prepared by a process comprising:
a) reacting the compounds of formula (VI) wherein R$_1$ is as described above with tert-butoxycarbonylanhydride, thus obtaining the compounds of formula (XIII) wherein R$_1$ is as described above (XII)

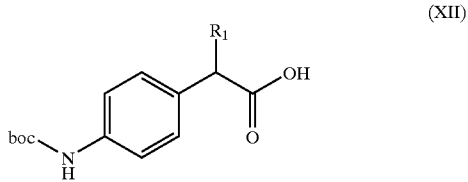

b) and by reacting the compounds of formula (XIII) with oxalyl or thionyl chloride.

The reaction between the compounds of formula (VI) with tertbutoxycarbonylanhydride can be carried out in a suitable solvent such as admixtures water/1,4-dioxane or water/dichloromethane admixtures, in the presence of a base such as sodium carbonate or sodium hydroxide, at a temperature ranging from about 0° C. to room temperature.

The reaction between the compounds of formula (XIII) with oxalyl or thionyl chloride can be carried out in a suitable solvent such as dichloromethane, tetrahydrofuran or ethyl acetate, in the presence of a catalytic amount of dimethylformamide at a temperature ranging from about 0° C. to reflux.

As it will be readily appreciated, if the compounds of formula (I), prepared according to the processes described above, are obtained as an admixture of isomers, their separation into the single isomers of formula (I), according to conventional techniques, is within the scope of the present invention.

Conventional techniques for resolution of the racemate include, for instance, partitioned crystallization of diastereoisomeric salt derivatives or preparative chiral HPLC.

Pharmacology

The compounds of formula (I) are active as cdk/cyclin inhibitors as they gave positive results when tested according to the following procedure.

The inhibiting activity of putative cdk/cyclin inhibitors and the potency of selected compounds was determined through a method of assay based on the use of the MultiScreen-PH 96 well plate (Millipore), in which phosphocellulose filter paper was placed at each well bottom allowing binding of positive charged substrate after a washing/filtration step.

When a radioactivity labelled phosphate moiety was transferred by the ser/threo kinase to the filter-bound histone, light emitted was measured in a scintillation counter.

The inhibition assay of cdk2/Cyclin A activity was performed according to the following protocol.

Kinase reaction: 1.5 $\mu$M histone H1 substrate, 25 $\mu$M ATP (0.5 uCi P33$\gamma$-ATP), 100 ng Cyclin A/cdk2 complex, 10 $\mu$M inhibitor in a final volume of 100 $\mu$l buffer (TRIS HCl 10 mM pH 7.5, MgCl$_2$ 10 mM, 7.5 mM DTT) were added to each well of a 96 U bottom well plate. After 10 minutes at 37° C. incubation, reaction was stopped by 20 µl EDTA 120 mM.

Capture: 100 µl were transferred from each well Multi-Screen plate, to allow substrate binding phosphocellulose filter. Plates were then washed 3 times with 150 µl/well PBS Ca++/Mg++ free and filtered by Multi-Screen filtration system.

Detection: filters were allowed to dry at 37° C., then 100 µl/well scintillant were added and 33P labelled histone H1 was detected by radioactivity counting in the Top-Count instrument.

Results: data were analysed and expressed as % inhibition referred to total activity of enzyme (=100%).

All compounds showing inhibition >50% were further analysed in order to study and define the kinetic-profile of the inhibitor via Ki calculation.

The protocol used was the same described above, except for ATP and substrate concentrations. Either the concentrate of ATP and histone H1 substrate were varied: 4, 8, 12, 24, 48 µM for ATP (containing proportionally diluted P33γ-ATP) and 0.4, 0.8, 1.2, 2.4, 4.8 µM for histone were used in absence and presence of two different, properly chosen inhibitor concentrations.

Experimental data were analysed by the computer program "SigmaPlot" for Ki determination, using a random bireactant system equation:

$$v = \frac{Vmax \frac{(A)(B)}{aK_AK_B}}{1 + \frac{(A)}{K_A} + \frac{(B)}{K_B} + \frac{(A)(B)}{aK_AK_B}}$$

where A=ATP and B=histone H1.

In addition, the inhibiting activity of putative cdk/cyclin inhibitors and the potency of selected compounds was determined using a method of assay based on the use of a SPA (Scintillation Proximity Assay) 96 well plate assay. The assay is based on the ability of streptavidin-coated SPA beads to capture a biotinylated peptide derived from a phosphorylation site of histone.

When a radioactivity labelled phosphate moiety was transferred by the serine/threonine kinase to the biotinylated histone peptide, light emitted was measured in scintillation counter.

The inhibition assay of cdk5/p25 activity was performed according to the following protocol.

Kinase reaction: 1.0 µM biotinylated histone peptide substrate, 0.25 uCi P33γ-ATP, 4 nM cdk2/p25 complex, 0–100 µM] inhibitor in a final volume of 100 µl buffer (Hepes 20 mM pH 7.5, MgCl$_2$ 15 mM, 1 mM DTT) were added to each well of a 96 U bottom well plate. After 20 min at 37° C. incubation, the reaction was stopped by the addition of 500 ug SPA beads in phosphate-buffered saline containing 0.1% Triton X-100, 50 M ATP and 5 mM EDTA. The beads were allowed to settle, and the radioactivity incorporated in the 33P-labelled peptide was detected in a Top Count scintillation counter.

Results: Data were analysed and expressed as % inhibition using the formula:

100×(1−(Unknown−*Bkgd*)/(Enz. Control−*Bkgd*))

IC50 values were calculated using a variation of the four parameter logistics equation:

$Y=100/[1+10^{(Log EC50-X)*Slope}]$

Where X=log(uM) and Y=% Inhibition.

Given the above inhibition assays, the compounds of formula (I) of the invention resulted to possess a remarkable cdk inhibitory activity and are thus useful in therapy against proliferative disorders associated with an altered cell cycle dependent kinase activity.

In particular, when tested against cdk2/A, the representative compound of the invention (2S)-N-(5-cyclopropyl-1H-pyrazol-3-yl)-2-[4-(2-oxo-1,3-oxazolidin-3-yl)phenyl]propanamide showed an inhibitory activity, expressed as IC$_{50}$, of 8 nM.

By restricting the unregulated proliferation of tumor cells, the compounds of formula (I) are therefore useful in therapy in the treatment of various tumors such as, for instance, carcinomas, e.g., mammary carcinoma, bladder carcinoma, colon carcinoma, ovary endometrial tumors, sarcomas, e.g., soft tissue and bone sarcomas, and the hematological malignancies such as, e.g., leukemias.

In addition, the compounds of formula (I) are also useful in the treatment of other cell proliferative disorders such as psoriasis, vascular smooth cell proliferation associated with atherosclerosis and post-surgical stenosis and restenosis, and in the treatment of Alzheimer's disease.

The compounds of the present invention can be administered either as single agents or, alternatively, in combination with known anticancer treatments such as radiation therapy or chemotherapy regimen in combination with cytostatic or cytotoxic agents, antibiotic-type agents, alkylating agents, antimetabolite agents, hormonal agents, immunological agents, interferon-type agents, cyclooxygenase inhibitors (e.g. COX-2 inhibitors), matrixmetalloprotease inhibitors, telomerase inhibitors, tyrosine kinase inhibitors, anti-growth factor receptor agents, anti-HER agents, anti-EGFR agents, anti-angiogenesis agents (e.g. angiogenesis inhibitors), farnesyl transferase inhibitors, ras-raf signal transduction pathway inhibitors, cell cycle inhibitors, other cdks inhibitors, tubulin binding agents, topoisomerase I inhibitors, topoisomerase II inhibitors, and the like.

As an example, the compounds of the invention can be administered in combination with one or more chemotherapeutic agents such as, for instance, exemestane, formestane, anastrozole, letrozole, fadrozole, taxane and derivatives such as paclitaxel or docetaxel, encapsulated taxanes, CPT-11, camptothecin derivatives, anthracycline glycosides, e.g., doxorubicin, idarubicin, epirubicin, etoposide, navelbine, vinblastine, carboplatin, cisplatin, estramustine, celecoxib, tamoxifen, raloxifen, Sugen SU-5416, Sugen SU-6668, Herceptin, and the like, optionally within liposomal formulations thereof.

If formulated as a fixed dose, such combination products employ the compounds of this invention within the dosage range described below and the other pharmaceutically active agent within the approved dosage range.

Compounds of formula (I) may be used sequentially with known anticancer agents when a combination formulation is inappropriate.

The compounds of formula (I) of the present invention, suitable for administration to a mammal, e.g., to humans, can be administered by the usual routes and the dosage level depends upon the age, weight, conditions of the patient and administration route.

For example, a suitable dosage adopted for oral administration of a compound of formula (I) may range from about 10 to about 500 mg per dose, from 1 to 5 times daily. The compounds of the invention can be administered in a variety of dosage forms, e.g., orally, in the form tablets, capsules, sugar or film coated tablets, liquid solutions or suspensions; rectally in the form suppositories; parenterally, e.g., intramuscularly, or through intravenous and/or intrathecal and/or intraspinal injection or infusion.

The present invention also includes pharmaceutical compositions comprising a compound of formula (I) or a pharmaceutically acceptable salt thereof in association with a pharmaceutically acceptable excipient, which may be a carrier or a diluent.

The pharmaceutical compositions containing the compounds of the invention are usually prepared following conventional methods and are administered in a suitable pharmaceutical form.

For example, the solid oral forms may contain, together with the active compound, diluents, e.g., lactose, dextrose saccharose, sucrose, cellulose, corn starch or potato starch; lubricants, e.g., silica, talc, stearic acid, magnesium or calcium stearate, and/or polyethylene glycols; binding agents, e.g., starches, arabic gum, gelatine methylcellulose, carboxymethylcellulose or polyvinyl pyrrolidone; disintegrating agents, e.g., starch, alginic acid, alginates or sodium starch glycolate; effervescing mixtures; dyestuffs; sweeteners; wetting agents such as lecithin, polysorbates, laurylsulphates; and, in general, non-toxic and pharmacologically inactive substances used in pharmaceutical formulations. These pharmaceutical preparations may be manufactured in known manner, for example, by means of mixing, granulating, tabletting, sugar-coating, or film-coating processes.

The liquid dispersions for oral administration may be, e.g., syrups, emulsions and suspensions.

As an example, the syrups may contain, as carrier, saccharose or saccharose with glycerine and/or mannitol and sorbitol.

The suspensions and the emulsions may contain, as examples of carriers, natural gum, agar, sodium alginate, pectin, methylcellulose, carboxymethylcellulose, or polyvinyl alcohol.

The suspension or solutions for intramuscular injections may contain, together with the active compound, a pharmaceutically acceptable carrier, e.g., sterile water, olive oil, ethyl oleate, glycols, e.g., propylene glycol and, if desired, a suitable amount of lidocaine hydrochloride.

The solutions for intravenous injections or infusions may contain, as a carrier, sterile water or preferably they may be in the form of sterile, aqueous, isotonic, saline solutions or they may contain propylene glycol as a carrier.

The suppositories may contain, together with the active compound, a pharmaceutically acceptable carrier, e.g., cocoa butter, polyethylene glycol, a polyoxyethylene sorbitan fatty acid ester surfactant or lecithin.

With the aim of better illustrating the present invention, without posing any limitation to it, the following examples are now given.

EXAMPLE 1

Tert-butyl-5-amino-3-cyclopropyl-1H-pyrazole-1-carboxylate (Method A) 0.81 g (6.6 mmol) of 3-cyclopropyl-1H-pyrazole-5-amine were dissolved in 20 ml of 2M sodium hydrate and 20 ml of dichloromethane. 2.8 g (13.2 mmol) of tert-butoxycarbonylanhydride were added and the mixture was maintained at room temperature under stirring overnight. The organic layer was separated, washed with water, dried over anhydrous sodium sulphate and evaporated. The title compound was crystallised from n-hexane (1 g, 71% yield).

ESI (+) MS: m/z 224 (100, MH+);

1H-NMR (400 MHz, DMSO-d6) ppm: 6.29 (s, 1H, H-pyrazole), 1.95 (m, 1H, CH-cyclopropyl), 1.46 (s, 9H, tert-butyl), 1.35–1.28 (2m, 4H, CH2-cyclopropyl).

According to the same method, but employing 3-cyclobutyl- or 3-cyclopentyl-1H-pyrazole-5-amine, the following compounds were prepared:
tertbutyl-5-amino-3-cyclobutyl-1H-pyrazole-1-carboxylate;

ESI (+) MS: m/z 238 (100, MH+);

1H-NMR (400 MHz, DMSO-d6) ppm: 6.27 (s, 1H, H-pyrazole), 2.71 (m, 1H, CH-cyclobutyl), 1.46 (s, 9H, tert-butyl), 2.00–2.34 (2m, 6H, CH2-cyclobutyl).

tertbutyl-5-amino-3-cyclopentyl-1H-pyrazole-1-carboxylate

ESI (+) MS: m/z 252 (100, MH+);

1H-NMR (400 MHz, DMSO-d6) ppm: 6.25 (s, 1H, H-pyrazole), 3.10 (m, 1H, CH-cyclopentyl), 1.46 (s, 9H, tert-butyl), 1.52–1.75 (2m, 8H, CH2-cyclopentyl).

(Method B) 1.09 g (10 mmol) of 3-cyclopropyl-3-oxopropanenitrile and 1.32 g (10 mmol) of tert-butylcarbazate in 25 ml of anhydrous ethanol were stirred at room temperature for 4 hours, then 0.5 ml of triethylamine were added at room temperature. After 3 days under stirring the solution was evaporated to dryness under reduced pressure. The resulting residue was taken up with 100 ml of n-hexane-ethylacetate 70/30 and stirred for 3 hours at 5° C. The solid was filtered through a Buchner funnel and then dried at 40° C. under vacuum yielding 2 g (90 %yield) of the title compound. Following the same method, but employing 3-cyclobutyl- or 3-cyclopentyl-oxopropanenitrile, tertbutyl-5-amino-3-cyclobutyl- or tertbutyl-5-amino-3-cyclopentyl-1H-pyrazole-1-carboxylate can be prepared.

EXAMPLE 2

2-(4-aminophenyl)propanoic-acid 10 g (0.05 mol) of 2-(4-nitrophenyl)propanoic acid were dissolved in a mixture of 5 ml of water and 100 ml of methanol and 0.65 g of Pd/C 5% were added. The mixture was submitted to hydrogenation at 60 psi for 2 hours at room temperature. After the separation of the catalyst by filtration on celite the methanol was evaporated under vacuum and the title compound was crystallised from water on cooling (7 g; 85 % yield).

ESI (+) MS: m/z 166 (100, MH+);

1H-NMR (400 MHz, DMSO-d6) ppm: 7.08–6.71 (2d, 4H, CH-phenyl, J=7.1 Hz), 3.76 (q, 1H, CH—Me, J=7.6 Hz), 1.53 (d, 3H, CH3, 7.6 Hz)

EXAMPLE 3

(2S)-2-(4-aminophenyl)propanoic acid and (2R)-2-(4-aminophenyl)propanoic acid

To 4.34 g of 2-(4-aminophenyl)propanoic acid, 26 ml of water and 3.94 g of L-(+)-tartaric acid were added. The mixture was heated at 80° C. under stirring until complete solution. Heating was then stopped and the solution made to spontaneously cool. After 24 hours 3.8 g of levorotatory tartrate were filtered and dried. The solution containing the dextrorotatory tartrate was concentrated under vacuum at 40° C. to evaporate about 10 ml of water. The solution was then cooled at 30° C. and 1.047 g of sodium hydrate were added. The (+)-(2S)-2-(4-aminophenyl)propanoic acid was collected by filtration and dried to give 1.36 g ($\alpha_D^{20}$=+73.0°; C=0.1% in methanol). Treating the levorotatory tartrate with sodium hydrate the (−)-(2R)-2-(4-aminophenyl)propanoic acid was obtained.

EXAMPLE 4

2-(4-{[(2-chloroethoxy)carbonyl]amino}phenyl)propanoic acid 1 g (6 mmol) of 2-(4-aminophenyl)propanoic acid was suspended in 30 ml of dichloromethane and 1.24 ml (12 mmol) of 2-chloroethylchloroformate were added at 0° C. under stirring. After 30 minutes at the same temperature 2.27 g (6 mmol) of sodium phosphate dodecahydrate were added portionwise. After 4 hours the reaction was complete (HPLC-MS). The mixture was made acidic by using hydrochloric acid 0.5N and the product extracted with dichloromethane. The organic layer was dried over sodium sulphate and evaporated under vacuum. 1.4 g (100%yield) of the title compound were obtained by crystallization from diisopropylether.

1H-NMR (400 MHz, DMSO-d6) ppm: 7.47–7.58 (2d, 4H, CH-phenyl, J=9.0 Hz), 3.75 (q, 1H, CH—Me, J=7.6 Hz), 4.31 (m, 2H, CH2Cl), 3.62 (m, 2H, CH2O), 1.53 (d, 3H, CH3, 7.6 Hz)

Analogously the following intermediates can be prepared starting from the suitable amino derivatives:

(2S)-2-(4-{[(2-chloroethoxy)carbonyl]amino}phenyl)propanoic acid;
(2R)-2-(4-{[(2-chloroethoxy)carbonyl]amino}phenyl)propanoic acid;
4-{[(2-chloroethoxy)carbonyl]amino}phenylacetic acid;

1H-NMR (400 MHz, DMSO-d6) ppm: 7.44–7.60 (2d, 4H, CH-phenyl, J=8.8 Hz), 3.43 (s, 2H, CH2Ph), 4.30 (m, 2H, CH2Cl), 3.63 (m, 2H, CH2O).

EXAMPLE 5

2-[4-(2-oxo-1,3-oxazolidin-3-yl)phenyl]propanoic acid 0.5 g (1.85 mmol) of 2-(4-{[(2-chloroethoxy)carbonyl]amino}phenyl)propanoic acid were dissolved in 10 ml of N,N-dimethylformamide and 0.45 g (3.7 mmol) of potassium carbonate were added. After 48 hours the solvent was evaporated under vacuum, the residue redissolved with dichloromethane and washed with hydrochloric acid 0.5 N. The organic layer was dried over sodium sulphate and evaporated. 0.35 g (80% yield) of the title compound crystallized from a mixture ethylacetate-diisopropylether.

ESI (+) MS: m/z 236 (100, MH+);

1H-NMR (400 MHz, DMSO-d6) ppm: 7.08–7.35 (2d, 4H, CH-phenyl, J=8.6 Hz), 3.76 (q, 1H, CH—Me, J=7.6 Hz), 3.80 (m, 2H, CH2N), 4.45 (m, 2H, CH2O), 1.53 (d, 3H, CH3, 7.6 Hz)

Analogously the following intermediates can be prepared starting from the suitable chloro derivatives:

(2R)-2-[4-(2-oxo-1,3-oxazolidin-3-yl)phenyl]propanoic acid;
(2S)-2-[4-(2-oxo-1,3-oxazolidin-3-yl)phenyl]propanoic acid;
4-(2-oxo-1,3-oxazolidin-3-yl)phenylacetic acid;
ESI (+) MS: m/z 222 (100, MH+);

1H-NMR (400 MHz, DMSO-d6) ppm: 7.10–7.38 (2d, 4H, CH-phenyl, J=8.7 Hz), 3.43 (s, 2H, CH2Ph), 3.79 (m, 2H, CH2N), 4.45 (m, 2H, CH2O).

EXAMPLE 6

N-(5-cyclopropyl-1H-pyrazol-3-yl)-2-[4-(2-oxo-1,3-oxazolidin-3-yl)phenyl]propanamide 3.36 g (14.3 mmol) of 2-[4-(2-oxo-1,3-oxazolidin-3-yl)phenyl]propanoic acid were suspended in 100 ml of dichloromethane. The mixture was cooled to 0° C. and 1.63 ml (18.67 mmol) of oxalyl chloride and 0.5 ml of N,N-dimethylformamide were added. After 3 hours at room temperature the solvent was evaporated. The resulting acyl chloride, without any further purification, was dissolved in 100 ml of tetrahydrofuran and added dropwise to a solution of 2.87 g (12.87 mmol) of tert-butyl-5-amino-3-cyclopropyl-1H-pyrazole-1-carboxylate and 16 ml (85.8 mmol) of N,N-diisopropylethylamine in 80 ml of tetrahydrofuran at 0° C. After 8 hours at room temperature, the solvent was evaporated, the residue redissolved in dichloromethane and washed with a saturated solution of sodium hydrogenocarbonate. The organic layer was dried over sodium sulphate and evaporated under vacuum. The resulting protected amide, without any further purification, was redissolved in 18 ml of dichloromethane and 2 ml of trifluoroacetic acid were added. After 3 hours at room temperature, the solvent was evaporated, the residue taken up with dichloromethane and washed with a sodium hydrogenocarbonate solution. The organic layer was dried over sodium sulfate and evaporated under vacuum. 2 g (41% yield overall) of the title compound were recovered after crystallization with diethylether-ethyl acetate.

ESI (+) MS: m/z 341 (100, MH+);

1H-NMR (400 MHz, DMSO-d6) ppm: 6.88 (m, 4H, CH-phenyl), 6.07 (s, 1H, CH-pyrazole), 3.82 (m, 2H, CH2N), 4.48 (m, 2H, CH2O), 3.85 (q, 1H, CHMe, J=6.8), 1.25 (d, 3H, CH3, J=6.8), 2.27 (m, 1H, CH-cyclopropyl), 1.28–1.35 (2d, 4H, CH2-cyclopropyl).

The following two compounds can be prepared by resolution of their racemic mixture, by chiral preparative HPLC (chiral cel OD; EtOH):

(2R)-N-(5-cyclopropyl-1H-pyrazol-3-yl)-2-[4-(2-oxo-1,3-oxazolidin-3-yl)phenyl]propanamide
(2S)-N-(5-cyclopropyl-1H-pyrazol-3-yl)-2-[4-(2-oxo-1,3-oxazolidin-3-yl)phenyl]propanamide Analogously the following compound can be prepared starting from the suitable carboxylic acid:
N-(5-cyclopropyl-1H-pyrazol-3-yl)-2-[4-(2-oxo-1,3-oxazolidin-3-yl)phenyl]acetamide
ESI (+) MS: m/z 327 (100, MH+);

1H-NMR (400 MHz, DMSO-d6) ppm: 6.92–7.60 (2d, 4H, CH-phenyl, J=8.8 Hz), 6.08 (s, 1H, CH-pyrazole), 3.70 (m, 2H, CH2N), 4.40 (m, 2H, CH2O), 3.68 (s, 2H, CH2Ph), 2.29 (m, 1H, CH-cyclopropyl), 1.26–1.34 (2d, 4H, CH2-cyclopropyl).

Analogously, but using tert-butyl-5-amino-3-cyclobutyl-1H-pyrazole-1-carboxylate the following compounds can be prepared starting from the suitable carboxylic acid:

N-(5-cyclobutyl-1H-pyrazol-3-yl)-2-[4-(2-oxo-1,3-oxazolidin-3-yl)phenyl]propanamide;
(2R)-N-(5-cyclobutyl-1H-pyrazol-3-yl)-2-[4-(2-oxo-1,3-oxazolidin-3-yl)phenyl]propanamide;

(2S)-N-(5-cyclobutyl-1H-pyrazol-3-yl)-2-[4-(2-oxo-1,3-oxazolidin-3-yl)phenyl]propanamide;
N-(5-cyclobutyl-1H-pyrazol-3-yl)-2-[4-(2-oxo-1,3-oxazolidin-3-yl)phenyl]acetamide;

Analogously, but using tert-butyl-5-amino-3-cyclopentyl-1H-pyrazole-1-carboxylate the following compounds can be prepared starting from the suitable carboxilic acid:

N-(5-cyclopentyl-1H-pyrazol-3-yl)-2-[4-(2-oxo-1,3-oxazolidin-3-yl)phenyl]propanamide;
(2R)-N-(5-cyclopentyl-1H-pyrazol-3-yl)-2-[4-(2-oxo-1,3-oxazolidin-3-yl)phenyl]propanamide;
(2S)-N-(5-cyclopentyl-1H-pyrazol-3-yl)-2-[4-(2-oxo-1,3-oxazolidin-3-yl)phenyl]propanamide;
N-(5-cyclopentyl-1H-pyrazol-3-yl)-2-[4-(2-oxo-1,3-oxazolidin-3-yl)phenyl]acetamide.

EXAMPLE 7

2-{4-[(tert-butoxycarbonyl)amino]phenyl}propanoic acid 12 g (73 mmol) of 2-(4-aminophenyl)propanoic acid were suspended in 140 mL of 1,4-dioxane and 140 mL of water and treated with 7.6 g (72 mmol) of sodium carbonate dissolved in 72 mL of water.

The resulting solution, cooled to 4° C., was treated with 17.2 g (79 mmol) of tert-butoxycarbonyl anhydride and stirred over night allowing the temperature to reach room temperature. The solvent was evaporated, the aqueous phase was washed with ethylacetate, diluted with the same solvent and treated under stirring with 1M potassium hydrogenosulphate. The organic layer was separated and extracted with ethylacetate. The combined organic extracts were washed with brine, dried over sodium sulphate and evaporated. 18.18 g (94% yield) of the title compound were obtained after trituration with hexane.

ESI (+) MS: m/z 266 (100, MH+);

1H-NMR (400 MHz, DMSO-d6) ppm: 7.47–7.52 (m, 4H, CH-phenyl), 3.76 (q, 1H, CHMe, J=7.6 Hz), 1.53 (d, 3H, CH3, J=7.6), 1 51 (s, 9H, tertbutyl).

Analogously the following compounds can be prepared starting from the suitable carboxylic acid:

(2R)-2-{4-[(tert-butoxycarbonyl)amino]phenyl}propanoic acid;
(2S)-2-{4-[(tert-butoxycarbonyl)amino]phenyl}propanoic acid;
2-{4-[(tert-butoxycarbonyl)amino]phenyl}acetic acid;

ESI (+) MS: m/z 252 (100, MH+);

1H-NMR (400 MHz, DMSO-d6) ppm: 7.45–7.51 (2d, 4H, CH-phenyl, J=8.8 Hz), 3.43 (s, 2H, CH2Ph), 1 51 (s, 9H, tertbutyl).

EXAMPLE 8 tert-butyl 5-[(2-{4-[(tert-butoxycarbonyl)amino]phenyl}propanoyl)amino]-3-cyclopropyl-1H-pyrazole-1-carboxylate 265 mg (1 mmol) of 2-{4-[(tert-butoxycarbonyl)amino]phenyl}propanoic acid were treated at 4° C. under nitrogen with 146 µl (2 mmol) of thionylchloride. The reaction mixture was stirred for 2.5 hours and the temperature was gradually raised to room temperature. The mixture was taken up with tetrahydrofuran and evaporated thoroughly. The resulting acyl chloride, without any further purification, was dissolved in 3 ml of dry tetrahydrofuran and added dropwise to a solution of 178 mg (0.8 mmol) of tert-butyl-5-amino-3-cyclopropyl-1H-pyrazole-1-carboxylate in 3 ml of tetrahydrofuran. 312 mg (1 mmol, loading 3.2 mmol/g) of polymer supported triethylamine were then added under stirring. After 2.5 hours 80 mg (loading 3.2 mmol/g) of polymer supported trisamine were finally added in order to quench the excess of acyl chloride. After 2 hours, the resins were filtered and washed with methanol and dichloromethane. Evaporation of the filtrate afforded 263 mg of the title compound as a foam (70% yield).

ESI (+) MS: m/z 471 (100, MH+);

1H-NMR (400 MHz, DMSO-d6) ppm: 7.04–7.13 (2d, 4H, CH-phenyl, J=8.5 Hz), 3.62 (s, 1H, CH-pyrazole), 3.73 (q, 1H, CHMe, J=6.9 Hz), 1.28 (d, 3H, CH3, J=6.9 Hz), 1.95 (m, 1H, CH-cyclopropyl), 1.26–1.36 (2d, 4H, CH2-cyclopropyl), 1.51 (s, 9H, tertbutyl-NH), 1.46 (s, 9H, tertbutyl-pyrazole).

Analogously the following compounds can be prepared starting from the suitable carboxylic acid:

(2R)-tert-butyl 5-[(2-{4-[(tert-butoxycarbonyl)amino]phenyl}propanoyl)amino]-3-cyclopropyl-1H-pyrazole-1-carboxylate;
(2S)-tert-butyl 5-[(2-{4-[(tert-butoxycarbonyl)amino]phenyl}propanoyl)amino]-3-cyclopropyl-1H-pyrazole-1-carboxylate;
tert-butyl 5-[(2-{4-[(tert-butoxycarbonyl)amino]phenyl}acetyl)amino]-3-cyclopropyl-1H-pyrazole-1-carboxylate.

Analogously, but using tert-butyl-5-amino-3-cyclobutyl-1H-pyrazole-1-carboxylate the following compounds can be prepared starting from the suitable carboxylic acid:

tert-butyl 5-[(2-{4-[(tert-butoxycarbonyl)amino]phenyl}propanoyl)amino]-3-cyclobutyl-1H-pyrazole-1-carboxylate;
(2R)-tert-butyl 5-[(2-{4-[(tert-butoxycarbonyl)amino]phenyl}propanoyl)amino]-3-cyclobutyl-1H-pyrazole-1-carboxylate;
(2S)-tert-butyl 5-[(2-{4-[(tert-butoxycarbonyl)amino]phenyl}propanoyl)amino]-3-cyclobutyl-1H-pyrazole-1-carboxylate;
tert-butyl 5-[(2-{4-[(tert-butoxycarbonyl)amino]phenyl}acetyl)amino]-3-cyclobutyl-1H-pyrazole-1-carboxylate.

Analogously, but using tert-butyl-5-amino-3-cyclopentyl-1H-pyrazole-1-carboxylate the following compounds can be prepared starting from the suitable carboxylic acid:

tert-butyl 5-[(2-{4-[(tert-butoxycarbonyl)amino]phenyl}propanoyl)amino]-3-cyclopentyl-1H-pyrazole-1-carboxylate;
(2R)-tert-butyl 5-[(2-{4-[(tert-butoxycarbonyl)amino]phenyl}propanoyl)amino]-3-cyclopentyl-1H-pyrazole-1-carboxylate;
(2S)-tert-butyl 5-[(2-{4-[(tert-butoxycarbonyl)amino]phenyl}propanoyl)amino]-3-cyclopentyl-1H-pyrazole-1-carboxylate;
tert-butyl 5-[(2-{4-[(tert-butoxycarbonyl)amino]phenyl}acetyl)amino]-3-cyclopentyl-1H-pyrazole-1-carboxylate.

EXAMPLE 9

2-(4-aminophenyl)-N-(5-cyclopropyl-1H-pyrazol-3-yl)propanamide 11.8 g (25.26 mmol) of tert-butyl 5-[(2-{4-[(tert-butoxycarbonyl)amino]phenyl}propanoyl)amino]-3- cyclopropyl-1H-pyrazole-1-carboxylate were dissolved in 200 ml of dichloromethane and 30 ml of trifluoroacetic acid were added. After 2.5 hours at room temperature the solvent was evaporated and the residue taken up with dichloromethane and washed with a saturated solution of sodium hydrogenocarbonate. The organic layer was then dried over sodium sulphate and evaporated to dryness, affording 4.7 g (70% yield) of the title compound.

ESI (+) MS: m/z 271 (100, MH+);

1H-NMR (400 MHz, DMSO-d6) ppm: 6.62 (s, 4H, CH-phenyl), 6.07 (s, 1H, CH-pyrazole), 3.82 (q, 1H, CHMe, J=6.8 Hz), 1.25 (d, 3H, CH3, J=6.8 Hz), 2.27 (m, 1H, CH-cyclopropyl), 1.28–1.35 (2d, 4H, CH2-cyclopropyl).

Analogously the following compounds can be prepared starting from the suitable carboxylic acid:

(2R)-2-(4-aminophenyl)-N-(5-cyclopropyl-1H-pyrazol-3-yl)propanamide;
(2S)-2-(4-aminophenyl)-N-(5-cyclopropyl-1H-pyrazol-3-yl)propanamide;
2-(4-aminophenyl)-N-(5-cyclopropyl-1H-pyrazol-3-yl)acetamide;

ESI (+) MS: m/z 258 (100, MH+);

1H-NMR (400 MHz, DMSO-d6) ppm: 6.61–7.34 (2d, 4H, CH-phenyl, J=8.8 Hz), 6.08 (s, 1H, CH-pyrazole), 3.67 (s, 2H, CH2Ph), 2.27 (m, 1H, CHcyclopropyl), 1.28–1.35 (2d, 4H, CH2-cyclopropyl).

Analogously, but using tert-butyl-5-amino-3-cyclobutyl-1H-pyrazole-1-carboxylate the following compounds can be prepared starting from the suitable carboxylic acid:

2-(4-aminophenyl)-N-(5-cyclobutyl-1H-pyrazol-3-yl)propanamide;
(2R)-2-(4-aminophenyl)-N-(5-cyclobutyl-1H-pyrazol-3-yl)propanamide;
(2S)-2-(4-aminophenyl)-N-(5-cyclobutyl-1H-pyrazol-3-yl)propanamide;
2-(4-aminophenyl)-N-(5-cyclobutyl-1H-pyrazol-3-yl)acetamide;

Analogously, but using tert-butyl-5-amino-3-cyclopentyl-1H-pyrazole-1-carboxylate the following compounds can be prepared starting from the suitable carboxylic acid:

2-(4-aminophenyl)-N-(5-cyclopentyl-1H-pyrazol-3-yl)propanamide;
(2R)-2-(4-aminophenyl)-N-(5-cyclopentyl-1H-pyrazol-3-yl)propanamide;
(2S)-2-(4-aminophenyl)-N-(5-cyclopentyl-1H-pyrazol-3-yl)propanamide;
2-(4-aminophenyl)-N-(5-cyclopentyl-1H-pyrazol-3-yl)acetamide.

EXAMPLE 10

2-chloroethyl 5-{[2-(4-{[(2-chloroethoxy)carbonyl]amino}phenyl)propanoyl]amino}-3-cyclopropyl-1H-pyrazole-1-carboxylate 154 mg (0.57 mmol) of 2-(4-aminophenyl)-N-(5-cyclopropyl-1H-pyrazol-3-yl)propanamide were dissolved in 1.9 ml of dry pyridine at 4° C. under argon atmosphere and 0.12 ml (1.148 mmol) of 2-chloroethylchloroformate were added dropwise. After 2.5 hours the reaction mixture was poured into ice and the precipitate solid collected by filtration, affording 225 mg (82% yield) of the title compound.

1H-NMR (400 MHz, DMSO-d6) ppm: 7.37–7.41 (m, 4H, CH-phenyl), 3.32 (s, 1H, CH-pyrazole), 3.85 (q, 1H, CHMe, J=6.8 Hz), 1.24 (d, 3H, CH3, J=6.8 Hz), 1.93 (m, 1H, CH-cyclopropyl), 1.27–1.35 (2d, 4H, CH2-cyclopropyl), 3.63–3.85 (m, 4H, CH2O), 4.30 (m, 4H, CH2Cl).

Analogously, but employing the suitable amide derivatives, the following compounds can be prepared:

2-chloroethyl 5-{[(2R)-2-(4-{[(2-chloroethoxy)carbonyl]amino}phenyl)propanoyl]amino}-3-cyclopropyl-1H-pyrazole-1-carboxylate;
2-chloroethyl 5-{[(2S)-2-(4-{[(2-chloroethoxy)carbonyl]amino}phenyl)propanoyl]amino}-3cyclopropyl-1H-pyrazole-1-carboxylate;
2-chloroethyl 5-{[2-(4-{[(2-chloroethoxy)carbonyl]amino}phenyl)acetyl]amino}-3-cyclopropyl-1H-pyrazole-1-carboxylate;
2-chloroethyl 5-{[(2R)-2-(4-{[(2-chloroethoxy)carbonyl]amino}phenyl)propanoyl]amino}-3-cyclobutyl-1H-pyrazole-1-carboxylate;
2-chloroethyl 5-{[(2S)-2-(4-{[(2-chloroethoxy)carbonyl]amino}phenyl)propanoyl]amino}-3-cyclobutyl-1H-pyrazole-1-carboxylate;
2-chloroethyl 5-{[2-(4-{[(2-chloroethoxy)carbonyl]amino}phenyl)propanoyl]amino}-3cyclobutyl-1H-pyrazole-1-carboxylate;
2-chloroethyl 5-{[2-(4-{[(2-chloroethoxy)carbonyl]amino}phenyl)acetyl]amino}-3-cyclobutyl-1H-pyrazole-1-carboxylate;
2-chloroethyl 5-{[(2S)-2-(4-{[(2-chloroethoxy)carbonyl]amino}phenyl)propanoyl]amino}-3-cyclopentyl-1H-pyrazole-1-carboxylate;
2-chloroethyl 5-{[(2-(4-{[(2chloroethoxy)carbonyl]amino}phenyl)propanoyl]amino}-3-cyclopentyl-1H pyrazole-1-carboxylate;
2-chloroethyl 5-{[2-(4-{[(2-chloroethoxy)carbonyl]amino}phenyl)acetyl]amino}-3-cyclopentyl-1H-pyrazole-1-carboxylate.

EXAMPLE 11

N-(3-cyclopropyl-1H-pyrazol-5-yl)-2-[4-(2-oxo-1,3-oxazolidin-3-yl)phenyl]propanamide 431 mg (0.89 mmol) of 2-chloroethyl 5-{[2-(4-{[(2-chloroethoxy)carbonyl]amino}phenyl)propanoyl]amino}-3cyclopropyl-1H-pyrazole-1-carboxylate were dissolved in 3 ml of N,N-dimethylformamide and 124 mg (0.89 mmol) of potassium carbonate were added and the mixture stirred at room temperature for 19 hours. The reaction mixture was poured into 30 ml of methanol and stirred for 40 minutes, evaporated under vacuum, diluted with 40 ml of methanol and washed with a saturated aqueous ammonium chloride solution. The organic layer was further extracted with dichloromethane, dried over sodium sulfate and evaporated to dryness. The crude was purified by chromatography on a silica gel column to afford 233 mg (77% yield) of the title compound. Analogously, but employing the suitable bisacylated amide derivatives, the following compounds can be prepared:

(2R)-N-(3-cyclopropyl-1H-pyrazol-5-yl)-2-[4-(2-oxo-1,3-oxazolidin-3-yl)phenyl]propanamide;
(2S)-N-(3-cyclopropyl-1H-pyrazol-5-yl)-2-[4-(2-oxo-1,3-oxazolidin-3-yl)phenyl]propanamide;
N-(3-cyclopropyl-1H-pyrazol-5-yl)-2-[4-(2-oxo-1,3-oxazolidin-3-yl)phenyl]acetamide;
(2R)-N-(3-cyclobutyl-1H-pyrazol-5-yl)-2-[4-(2-oxo-1,3-oxazolidin-3-yl)phenyl]propanamide;

(2S)-N-(3-cyclobutyl-1H-pyrazol-5-yl)-2-[4-(2-oxo-1,3-oxazolidin-3-yl)phenyl]propanamide;
N-(3-cyclobutyl-1H-pyrazol-5-yl)-2-[4-(2-oxo-1,3-oxazolidin-3-yl)phenyl]propanamide
N-(3-cyclobutyl-1H-pyrazol-5-yl)-2-[4-(2-oxo-1,3-oxazolidin-3-yl)phenyl]acetamide;
N-(3-cyclopentyl-1H-pyrazol-5-yl)-2-[4-(2-oxo-1,3-oxazolidin-3-yl)phenyl]propanamide
(2R)-N-(3-cyclopentyl-1H-pyrazol-5-yl)-2-[4-(2-oxo-1,3-oxazolidin-3-yl)phenyl]propanamide;
(2S)-N-(3-cyclopentyl-1H-pyrazol-5-yl)-2-[4-(2-oxo-1,3-oxazolidin-3-yl)phenyl]propanamide;
N-(3-cyclopentyl-1H-pyrazol-5-yl)-2-[4-(2-oxo-1,3-oxazolidin-3-yl)phenyl]acetamide.

What is claimed is:

1. A method for treating a cell proliferative disorder associated with an altered cell cycle dependent kinase activity comprising:

administering to a mammal in need thereof an effective amount of a phenylacetamido-pyrazole compound represented by formula (I):

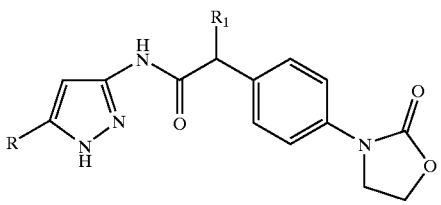

wherein
R is a $C_3$–$C_5$ cycloalkyl group;
$R_1$ is a hydrogen atom or a methyl group; or a pharmaceutically acceptable salt thereof.

2. The method according to claim 1 wherein the cell proliferative disorder is selected from the group consisting of cancer, Alzheimer's disease, a viral infection, an autoimmune disease and a neurodegenerative disorder.

3. The method according to claim 2 comprising treating a cancer selected from the group consisting of carcinoma, squamous cell carcinoma, a hematopoietic tumor of myeloid or lymphoid lineage, a tumor of mesenchymal origin, a tumor of the central or peripheral nervous system, melanoma, seminoma, teratocarcinoma, osteosarcoma, xeroderma pigmentosum, keratocanthoma, thyroid follicular cancer, and Kaposi's sarcoma.

4. The method of claim 1, wherein the cell proliferative disorder is selected from the group consisting of benign prostate hyperplasia, familial adenomatosis polyposis, neuro-fibromatosis, psoriasis, vascular smooth cell proliferation associated with atherosclerosis, pulmonary fibrosis, arthritis, glomerulonephritis and post-surgical stenosis and/or restenosis.

5. The method of claim 1, further comprising subjecting the mammal to a radiation therapy and/or a chemotherapy regimen.

6. The method of claim 1 that comprises treating a human.

7. A method according to claim 1 that comprises administering an effective amount of the compound of formula (I) that is (2S)-N-(5-cyclopropyl-1H-pyrazol-3-yl)-2-[4-(2-oxo-1,3-oxazolidin-3-yl)phenyl]propanamide.

8. A phenylacetamido-pyrazole compound represented by formula (I):

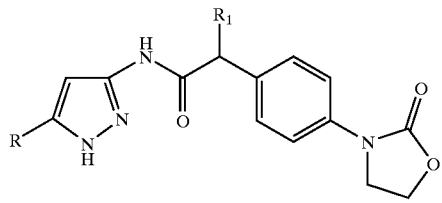

wherein
R is a $C_3$–$C_5$ cycloalkyl group;
$R_1$ is a hydrogen atom or a methyl group;
or a pharmaceutically acceptable salt thereof.

9. The compound of claim 8, wherein R is cyclopropyl.

10. The compound of claim 8, wherein $R_1$ is methyl.

11. The compound of claim 8, wherein R is cyclopropyl and $R_1$ is methyl.

12. The compound of claim 11 that is (2S)-N-(5-cyclopropyl-1H-pyrazol-3-yl)-2-[4-(2-oxo-1,3-oxazolidin-3-yl)phenyl]propanamide.

13. The compound of claim 8, optionally in the form of a pharmaceutically acceptable salt, selected from the group consisting of:

N-(5-cyclopropyl-1H-pyrazol-3-yl)-2-[4-(2-oxo-1,3-oxazolidin-3-yl)phenyl]propanamide;
(2R)-N-(5-cyclopropyl-1H-pyrazol-3-yl)-2-[4-(2-oxo-1,3-oxazolidin-3-yl)phenyl]propanamide;
(2S)-N-(5-cyclopropyl-1H-pyrazol-3-yl)-2-[4-(2-oxo-1,3-oxazolidin-3-yl)phenyl]propanamide
N-(5-cyclopropyl-1H-pyrazol-3-yl)-2-[4-(2-oxo-1,3-oxazolidin-3-yl)phenyl]acetamide;
N-(5-cyclobutyl-1H-pyrazol-3-yl)-2-[4-(2-oxo-1,3-oxazolidin-3-yl)phenyl]propanamide;
(2R)-N-(5-cyclobutyl-1H-pyrazol-3-yl)-2-[4-(2-oxo-1,3-oxazolidin-3-yl)phenyl]propanamide;
(2S)-N-(5-cyclobutyl-1H-pyrazol-3-yl)-2-[4-(2-oxo-1,3-oxazolidin-3-yl)phenyl]propanamide;
N-(5-cyclobutyl-1H-pyrazol-3-yl)-2-[4-(2-oxo-1,3-oxazolidin-3-yl)phenyl]acetamide;
N-(5-cyclopentyl-1H-pyrazol-3-yl)-2-[4-(2-oxo-1,3-oxazolidin-3-yl)phenyl]propanamide;
(2R)-N-(5-cyclopentyl-1H-pyrazol-3-yl)-2-[4-(2-oxo-1,3-oxazolidin-3-yl)phenyl]propanamide;
(2S)-N-(5-cyclopentyl-1H-pyrazol-3-yl)-2-[4-(2-oxo-1,3-oxazolidin-3-yl)phenyl]propanamide; and
N-(5-cyclopentyl-1H-pyrazol-3-yl)-2-[4-(2-oxo-1,3-oxazolidin-3-yl)phenyl]acetamide.

14. A process for preparing a compound of claim 8 that comprises:

a) reacting a compound of formula (II) or the regioisomer of formula (IIa):

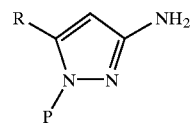

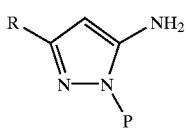

(IIa)

wherein R is as defined in claim 8 and P represents a suitable nitrogen-pyrazole protecting group, with a compound of formula (III):

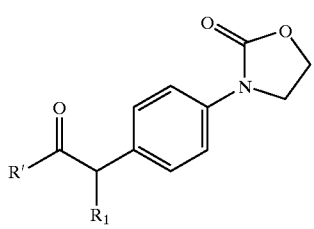

(III)

wherein $R_1$ is as defined in claim 11 and R' represents hydroxy or a halogen atom, thus obtaining a compound of formula (IV) or (IVa):

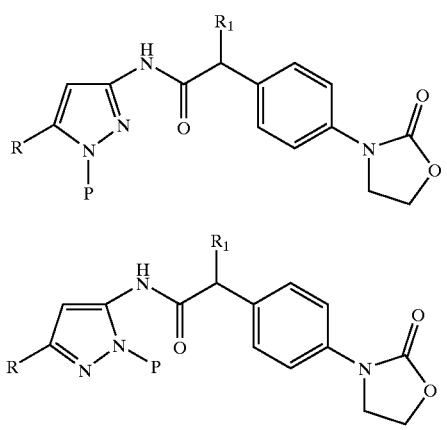

(IV)

(IVa)

b) and deprotecting the compound of formula (IV) or (IVa) so as to obtain the compound of formula (I) and, if desired, converting said compound of formula (I) into a pharmaceutically acceptable salt.

15. The process of claim 14 wherein, within the compound of formula (II) or (IIa), P represents a tert-butoxycarbonyl group.

16. The process of claim 14 wherein, within the compound of formula (III), R' is hydroxy or a chlorine atom.

17. A pharmaceutical composition comprising the compound of claim 8, and at least one pharmaceutically acceptable excipient, carrier and/or diluent.

18. The pharmaceutical composition of claim 17, further comprising one or more chemotherapeutic agent(s).

19. A product or kit comprising the compound of claim 8 or a pharmaceutical composition comprising the compound of claim 8.

20. The product or kit of claim 19, further containing one or more chemotherapeutic agent(s).

21. The product or kit of claim 20, wherein said compound or composition, and said chemotherapeutic agent(s) are formulated for simultaneous, separate or sequential use in anticancer therapy.

22. A method for making a medicament or a pharmaceutical composition comprising:

admixing a compound of claim 8 with a pharmaceutically acceptable carrier, diluent or excipient, and optionally with one or more chemotherapeutic agent(s).

23. A method for inhibiting cyclin dependent kinase activity comprising contacting a cyclin dependent kinase with an effective amount of the compound of claim 8.

24. A method for treating a tumor or cancer comprising administering to a subject in need thereof an effective amount of the compound of claim 8.

25. A method for treating a cell proliferative disorder comprising administering to a subject in need thereof an effective amount of the compound of claim 8.

26. A method for treating Alzheimer's Disease comprising administering to a subject in need thereof an effective amount of the compound of claim 8.

27. A method for modulating a disease associated with apoptosis comprising administering to a subject in need thereof an effective amount of the compound of claim 8.

28. A method for inhibiting angiogenesis comprising administering to a subject in need thereof an effective amount of the compound of claim 8.

29. A method for inhibiting metastasis comprising administering to a subject in need thereof an effective amount of the compound of claim 8.

30. A method for inhibiting a disease associated with a protein kinase comprising administering an effective amount of the compound of claim 8 to a subject in need thereof.

31. A method for treating alopecia comprising administering to a subject in need thereof an effective amount of the compound of claim 8.

* * * * *